(12) United States Patent
Zhu et al.

(10) Patent No.: US 10,105,408 B2
(45) Date of Patent: Oct. 23, 2018

(54) TRADITIONAL CHINESE MEDICINE COMPOSITION AND PREPARATION METHOD AND USE THEREOF

(71) Applicant: INFINITUS (CHINA) COMPANY LTD., Jiang Men (CN)

(72) Inventors: Huawei Zhu, Jiang Men (CN); Jialing Ning, Jiang Men (CN); Yiting Yang, Jiang Men (CN); Shuo Liu, Jiang Men (CN); Chung Wah Ma, Jiang Men (CN)

(73) Assignee: INFINITUS (CHINA) COMPANY LTD., Jiang Men (CN)

( * ) Notice: Subject to any disclaimer, the term of this patent is extended or adjusted under 35 U.S.C. 154(b) by 0 days.

(21) Appl. No.: 15/483,402

(22) Filed: Apr. 10, 2017

(65) Prior Publication Data
US 2018/0085416 A1  Mar. 29, 2018

(30) Foreign Application Priority Data
Sep. 27, 2016 (CN) .......................... 2016 1 0855443

(51) Int. Cl.
| | | |
|---|---|---|
| *A61K 36/00* | (2006.01) | |
| *A61K 36/752* | (2006.01) | |
| *A61K 36/288* | (2006.01) | |
| *A61K 36/484* | (2006.01) | |
| *A61K 36/346* | (2006.01) | |
| *A61K 36/185* | (2006.01) | |
| *A23G 3/48* | (2006.01) | |
| *A23L 33/00* | (2016.01) | |
| *A23L 33/105* | (2016.01) | |

(52) U.S. Cl.
CPC .............. *A61K 36/752* (2013.01); *A23G 3/48* (2013.01); *A23L 33/105* (2016.08); *A23L 33/40* (2016.08); *A61K 36/185* (2013.01); *A61K 36/288* (2013.01); *A61K 36/346* (2013.01); *A61K 36/484* (2013.01); *A23V 2002/00* (2013.01); *A61K 2236/331* (2013.01); *A61K 2236/53* (2013.01)

(58) Field of Classification Search
CPC ....................................................... A61K 36/00
See application file for complete search history.

*Primary Examiner* — Qiuwen Mi
(74) *Attorney, Agent, or Firm* — Parker Highlander PLLC

(57) ABSTRACT

The present invention relates to the field of traditional Chinese medicine formulation, particularly to a composition and the preparation method and use thereof. The traditional Chinese medicine composition provided by the present invention is produced from raw materials comprising TARAXACI HERBA, GLYCYRRHIZAE RADIX ET RHIZOMA, PLATYCODONIS RADIX, CITRI RETICULATAE PERICARPIUNM and PHYLLANTHI FRUCTUS. The traditional Chinese medicine composition adopts fewer herb medicines. By reasonable combination, the various herbal medicines mutually reinforce in terms of the effects of clearing throat, anti-inflammation and reducing phlegm, exhibit obvious synergistic effect. Pharmacological tests and clinical trials indicate that the traditional Chinese medicine composition has significant throat clear, anti-inflammatory, expectorant effects ($p<0.05$), and has no obvious toxic and side effects.

3 Claims, No Drawings

TRADITIONAL CHINESE MEDICINE COMPOSITION AND PREPARATION METHOD AND USE THEREOF

CROSS REFERENCE TO RELATED APPLICATIONS

The present application claims the priority of Chinese Patent Application No. 201610855443.8, as filed on Sep. 27, 2016 and titled with "TRADITIONAL CHINESE MEDICINE COMPOSITION AND PREPARATION METHOD AND USE THEREOF," and the disclosure of which is incorporated herein by reference.

FIELD

The present invention relates to the field of traditional Chinese medicine formulation, particularly to a traditional Chinese medicine composition and the preparation method and use thereof.

BACKGROUND

Throat, as an important physiological organ of human body, has long been known as the "the first gate" of human body. It is closely related to the life activities of many systems, such as the digestive system, respiratory system and immune system; all of them can not be separated from the role of the throat. It can not only help the human body in blocking a number of bacteria outside and protect human health, but also involve in the functions such as swallowing, breathing, pronunciation, etc. But in real life, it is easy to be affected by a variety of external physical and chemical factors, biological factors, leading to inflammation of the mucous membrane of the pharynx, and producing laryngopharyngitis. It belongs to the throat discomfort category such as "pharynx paralyzation" and "laryngeal aphonia" in traditional Chinese medicine and pharyngitis, laryngitis in modern medicine.

Throat discomfort can be divided into pharyngeal discomfort and throat discomfort. Its pathological basis is mainly the acute and chronic inflammations of pharyngeal mucosa, submucosa and lymphoid tissue, caused by infection factors such as bacteria (such as A type *Streptococcus*) and virus, vocal fatigue and unscientific pronunciation, excessive alcohol and tobacco consumption and other non-infectious factors such as spicy stimulation. Its usual manifestation is such phenomena as dry throat and throat itching, dry cough, sore throat, cough with phlegm, foreign body sensation, increased pharyngeal secretion and easy nausea. The throat discomfort is mainly manifested by hoarseness, heavy and rough voice. Accompanied by hoarseness, increased throat secretions and dry throat will appear. And the patients often feel phlegm adhesion; whenever talking, they will feel sore in the throat, and have to cough to remove viscous phlegm.

At present, there are a lot of Chinese herbal medicine combinations for the treatment of pharyngitis, but they all contain much more ingredients and have complicated constitutions. For example, patent CN101721614 discloses a pharmaceutical composition having the efficacy of clearing throat and relieving swelling and pain, consisting of thirteen herb medicines such as honeysuckle, ophiopogon root, dried rehmannia root, radix sophorae tonkinensis, etc. Patent CN104225289 discloses a traditional Chinese medicine for treating pharyngitis, consisting of seventeen herb medicines such as polygonatum odorati, tremella, Radix Scutellariae, Radix Sophorae Flavescentis, etc.

SUMMARY

In view of this, the objective of the present invention is to provide a traditional Chinese medicine composition having fewer herb medicines, simple ingredients, good anti-inflammatory and expectorant effects and the preparation method and use thereof.

To realize the objective of the present invention, the present invention adopts the following technical solutions:

The present invention provides a traditional Chinese medicine composition, produced from raw materials comprising TARAXACI HERBA, GLYCYRRHIZAE RADIX ET RHIZOMA, PLATYCODONIS RADIX, CITRI RETICULATAE PERICARPIUNM and PHYLLANTHI FRUCTUS.

In accordance with the theory of traditional Chinese medicine, the present invention reasonably combines TARAXACI HERBA, GLYCYRRHIZAE RADIX ET RHIZOMA, PLATYCODONIS RADIX, CITRI RETICULATAE PERICARPIUNM and PHYLLANTHI FRUCTUS. In the selected traditional Chinese medicine components, TARAXACI HERBA clears away heat and toxic materials, relieves swelling and benefits pharynx; PLATYCODONIS RADIX, as the monarch drug, has a bitter, spicy but mild taste, acts on lung channel, has the functions of opening the inhibited lung-energy and eliminating the evil from the interior to superficies and benefiting the throat; the combined medicine PHYLLANTHI FRUCTUS, as the ministerial drug, has a bitter, sweet, sour taste and is cool-natured, has the functions of clears away heat materials and benefits pharynx, promoting fluid and reducing phlegm; CITRI RETICULATAE PERICARPIUNM has a spicy and bitter taste and is warm-natured, has a fragrant smell, acts on spleen and lung channels. Because of its spicy taste, CITRI RETICULATAE PERICARPIUNM can dissipate stagnation of Qi; because of its bitter and warm nature, CITRI RETICULATAE PERICARPIUNM can dissipate the cold and dry the wet. Therefore, CITRI RETICULATAE PERICARPIUNM is an important medicine for regulating the flow of Qi, drying the wet, reducing phlegm, which can adjust the Qi activities of lung and stomach, reduce phlegm and dissipate stagnation to facilitate the throat; GLYCYRRHIZAE RADIX ET RHIZOMA is sweet and flat natured, can not only detoxify but also clear heat. Thus, CITRI RETICULATAE PERICARPIUNM and GLYCYRRHIZAE RADIX ET RHIZOMA are both functioned as adjuvant drug. GLYCYRRHIZAE RADIX ET RHIZOMA has the function of coordinating the drug actions based on its sweet taste, also functioned as the conductant drug. Various drugs in combination play the function of clearing throat, phlegm, Qi effect, adjusting Qi and relieving phlegm.

Among them, preferably, calculated on the basis of part by weight, the raw materials comprise:

| | |
|---|---|
| TARAXACI HERBA | 10-100 parts; |
| GLYCYRRHIZAE RADIX ET RHIZOMA | 10-100 parts; |
| PLATYCODONIS RADIX | 5-50 parts; |
| CITRI RETICULATAE PERICARPIUNM | 5-50 parts; |
| PHYLLANTHI FRUCTUS | 5-50 parts. |

More preferably, calculated on the basis of part by weight, the raw materials comprise:

| | |
|---|---|
| TARAXACI HERBA | 20-70 parts; |
| GLYCYRRHIZAE RADIX ET RHIZOMA | 20-70 parts; |
| PLATYCODONIS RADIX | 10-35 parts; |
| CITRI RETICULATAE PERICARPIUNM | 10-35 parts; |
| PHYLLANTHI FRUCTUS | 10-35 parts. |

More preferably, calculated on the basis of part by weight, the raw materials comprise:

| | |
|---|---|
| TARAXACI HERBA | 50 parts; |
| GLYCYRRHIZAE RADIX ET RHIZOMA | 50 parts; |
| PLATYCODONIS RADIX | 25 parts; |
| CITRI RETICULATAE PERICARPIUNM | 25 parts; |
| PHYLLANTHI FRUCTUS | 25 parts. |

Meanwhile, in the specific embodiments of the present invention, calculated on the basis of part by weight, the raw materials can also be selected as:

TARAXACI HERBA 20 parts, GLYCYRRHIZAE RADIX ET RHIZOMA 70 parts, PLATYCODONIS RADIX 10 parts, CITRI RETICULATAE PERICARPIUNM 35 parts, PHYLLANTHI FRUCTUS 10 parts;

TARAXACI HERBA 70 parts, GLYCYRRHIZAE RADIX ET RHIZOMA 20 parts, PLATYCODONIS RADIX 35 parts, CITRI RETICULATAE PERICARPIUNM 10 parts, PHYLLANTHI FRUCTUS 35 parts;

TARAXACI HERBA 100 parts, GLYCYRRHIZAE RADIX ET RHIZOMA 20 parts, PLATYCODONIS RADIX 10 parts, CITRI RETICULATAE PERICARPIUNM 10 parts, PHYLLANTHI FRUCTUS 20 parts;

TARAXACI HERBA 50 parts, GLYCYRRHIZAE RADIX ET RHIZOMA 70 parts, PLATYCODONIS RADIX 20 parts, CITRI RETICULATAE PERICARPIUNM 20 parts, PHYLLANTHI FRUCTUS 10 parts;

TARAXACI HERBA 30 parts, GLYCYRRHIZAE RADIX ET RHIZOMA 60 parts, PLATYCODONIS RADIX 30 parts, CITRI RETICULATAE PERICARPIUNM 15 parts, PHYLLANTHI FRUCTUS 15 parts.

The present invention also provides a method for preparing the traditional Chinese medicine compositions referred in the above technical solutions: subjecting TARAXACI HERBA, GLYCYRRHIZAE RADIX ET RHIZOMA, PLATYCODONIS RADIX, CITRI RETICULATAE PERICARPIUNM and PHYLLANTHI FRUCTUS to mixing, water extraction, alcohol precipitation to obtain the traditional Chinese medicine compositions.

Preferably, water extraction is performed for 2-3 times; every time, the water extraction time is 1-3 h; every time, the amount of added water during water extraction is 7-15 times of the mass of raw materials. In some Examples of the present invention, water extraction is performed for twice, 10 times water is added for the first time, boiled for 1.5 h; 8 times water is added for the second time, boiled for 1 h.

Preferably, after water extraction and before alcohol precipitation, the preparation method further comprises the step of:

pooling and filtering the water extract and concentrating the filtrate to a concentrate with a solid content of 20-50% at 20° C. under reduced pressure.

In some specific embodiments of the present invention, after water extraction and before alcohol precipitation, the preparation method further comprises:

pooling and filtering the water extract and concentrating the filtrate to a concentrate with a solid content of 30% at 20° C.

In some specific embodiments of the present invention, the alcohol precipitation is performed by adding ethanol to an ethanol concentration of 50-80%, standing for 24 h or more, discarding the filtration residue, concentrating the supernatant to an extractum with a solid content of 60-85%. The extractum is the traditional Chinese medicine composition of the present application. Preferably, adding ethanol until an ethanol concentration of 60%, standing for above 24 h, discarding the filter residue, concentrating the supernatant to an extractum with a solid content of 80%.

The present invention further provides a traditional Chinese medicine formulation for clearing throat and anti-inflammation, comprising the traditional Chinese medicine composition produced by the preparation method provided by the present invention or the traditional Chinese medicine composition provided by the present invention and a pharmaceutically acceptable carrier; preferably, the traditional Chinese medicine formulation is in the form of ointment, granules, pill, powder, tablet, capsule or oral liquid. The carrier and dosage forms well-known by a person skilled in the art are all within the protection scope of the present invention. The present invention is not limited thereto.

The present invention further provides a candy for clearing and nourishing throat, comprising the traditional Chinese medicine composition produced by the preparation method provided by the present invention or the traditional Chinese medicine composition provided by the present invention and an acceptable raw materials of food additive; the candy is hard candy or soft candy. Preferably, the excipients are selected from one or more of sucrose, glucose, fructose syrup, maltitol, xylitol, isomaltitol, flavors and fragrances, or from one or more of gelatin, pectin, carrageenan, syrup, flavors and fragrances.

The traditional Chinese medicine composition of the present invention, produced from the raw materials comprising TARAXACI HERBA, GLYCYRRHIZAE RADIX ET RHIZOMA, PLATYCODONIS RADIX, PHYLLANTHI FRUCTUS and CITRI RETICULATAE PERICARPIUNM, has fewer herb medicines, simple ingredients. By reasonable combination, the various herbal medicines of present invention mutually reinforce in terms of the effects of clearing throat, anti-inflammation and reducing phlegm, exhibit obvious synergistic effect. Pharmacological tests and clinical trials indicate that the traditional Chinese medicine composition has significant anti-inflammatory, expectorant effects ($p<0.05$), and has no obvious toxic and side effects.

DETAILED DESCRIPTION

The present invention discloses a traditional Chinese medicine composition and the preparation method and use thereof. A person skilled in the art can realize it by referring to the content herein and appropriately improve the technical parameters. It is particularly important to note that all of the similar replacements and changes are obvious to a person skilled in the art and are comprised within the present invention. The method and use of the present invention have been described by the preferred embodiments. Related persons can obviously alter or appropriately change and combine the method and use of the present invention to implement and use the technology of the present invention without departing from the content, spirit and scope of the present invention.

The present invention provides a composition and the preparation method and use thereof. Components and reagents can be purchased in the market. Through the conventional preparation process, it can be made into various pharmaceutical dosage forms, such as . . . It is not defined here.

Experimental drugs: Dexamethasone is purchased from GuangDong HuaNan Pharmacy Ltd., with the national medicine permission number H44024469;

ammonium chloride is purchased from Guangzhou Xinjian Fine Chemical Co., Ltd, batch number: 041203;

lipopolysaccharide (LPS) is purchased from sigma, the USA.

Experimental animal: Male SD rats (about 8 weeks old), Balb/c male mice (about 8 weeks old), all provided by experimental animal department of the Hong Kong University of Science and Technology.

The present invention is further described in connection with Examples:

Example 1 Traditional Chinese Medicine Composition of the Present Invention

1. Raw Materials

TARAXACI HERBA 50 parts, GLYCYRRHIZAE RADIX ET RHIZOMA parts, PLATYCODONIS RADIX 25 parts, CITRI RETICULATAE PERICARPIUNM 25 parts, PHYLLANTHI FRUCTUS 25 parts.

2. Preparation Method

The raw materials of TARAXACI HERBA, GLYCYRRHIZAE RADIX ET RHIZOMA, PLATYCODONIS RADIX, CITRI RETICULATAE PERICARPIUNM and PHYLLANTHI FRUCTUS were mixed, boiled for twice with the addition of water. 10 times water was added for the first time, boiled for 1.5 h; 8 times water was added for the second time, boiled for 1 h. The water extraction liquid was combined, filtered, and the filtrate was concentrated to a Chinese herbal medicine concentrated liquid with a solid content of 30% at 20° C. Ethanol was added until an ethanol concentration of 60%, standed for above 24 h, the filter residue was discarded, and the supernatant was concentrated to a Chinese herbal medicine extractum with a solid content of 80%, which is the traditional Chinese medicine composition of the present application.

Example 2 Traditional Chinese Medicine Composition of the Present Invention

1. Raw Materials

TARAXACI HERBA 20 parts, GLYCYRRHIZAE RADIX ET RHIZOMA parts, PLATYCODONIS RADIX 10 parts, CITRI RETICULATAE PERICARPIUNM 35 parts, PHYLLANTHI FRUCTUS 10 parts.

2. Preparation Method: The Same as Example 1

Example 3 Traditional Chinese Medicine Composition of the Present Invention

1. Raw Materials

TARAXACI HERBA 70 parts, GLYCYRRHIZAE RADIX ET RHIZOMA 20 parts, PLATYCODONIS RADIX 35 parts, CITRI RETICULATAE PERICARPIUNM 10 parts, PHYLLANTHI FRUCTUS 35 parts.

2. Preparation Method

TARAXACI HERBA, GLYCYRRHIZAE RADIX ET RHIZOMA, PLATYCODONIS RADIX, CITRI RETICULATAE PERICARPIUNM, PHYLLANTHI FRUCTUS were mixed, boiled for three times with the addition of water. 12 times water was added for the first time, boiled for 3 h; 8 times water was added for the second time, boiled for 2 h; 7 times water was added for the third time, boiled for 2 h. The water extraction liquid was combined, filtered, and the filtrate was concentrated to a Chinese herbal medicine concentrated liquid with a solid content of 35% at 20° C. Ethanol was added until an ethanol concentration of 70%, standed for above 24 h, the filter residue was discarded, and the supernatant was concentrated to a Chinese herbal medicine extractum with a solid content of 60%, which is the traditional Chinese medicine composition of the present application.

Example 4 Traditional Chinese Medicine Composition of the Present Invention

1. Raw Materials

TARAXACI HERBA 100 parts, GLYCYRRHIZAE RADIX ET RHIZOMA 20 parts, PLATYCODONIS RADIX 10 parts, CITRI RETICULATAE PERICARPIUNM 10 parts, PHYLLANTHI FRUCTUS 20 parts;

2. Preparation Method: The Same as Example 2

Example 5 Traditional Chinese Medicine Composition of the Present Invention

1. Raw Materials

TARAXACI HERBA 50 parts, GLYCYRRHIZAE RADIX ET RHIZOMA 70 parts, PLATYCODONIS RADIX 20 parts, CITRI RETICULATAE PERICARPIUNM 20 parts, PHYLLANTHI FRUCTUS 10 parts;

2. Preparation Method: The Same as Example 1

Example 6 Traditional Chinese Medicine Composition of the Present Invention

1. Raw Materials

TARAXACI HERBA 30 parts, GLYCYRRHIZAE RADIX ET RHIZOMA 60 parts, PLATYCODONIS RADIX 30 parts, CITRI RETICULATAE PERICARPIUNM 15 parts, PHYLLANTHI FRUCTUS 15 parts;

2. Preparation Method: The Same as Example 2

Comparative Example 1 Traditional Chinese Medicine Composition

Comparative Example 1 of the present invention provides a traditional Chinese medicine composition produced by the components having the following part by weight ratio: TARAXACI HERBA 60 parts, GLYCYRRHIZAE RADIX ET RHIZOMA 60 parts, PLATYCODONIS RADIX 30 parts, CITRI RETICULATAE PERICARPIUNM 30 parts.

The preparation method thereof is identical to that of Example 1, except for the constitution of raw materials.

Example 7: Effect on Acute Pharyngitis (Capsaicin Induced Pharyngitis)

Experimental method: 90 male SD rats (~8 weeks age) were randomized into 9 groups (10 rats/group). The groups were respectively blank control group, model group and positive control groups—dexamethasone group, low, medium and high dose groups of the traditional Chinese medicine composition produced by Comparative Example 1 (0.18, 0.53, 1.05 ml/kg), low, medium and high dose groups of the medicament produced by Example 1 (0.18, 0.53, 1.05 ml/kg). Animals from Comparative Example groups and Example of the present application groups were intragastrically administrated 30 days before modeling, once a day. Blank control group and model control group were administered equal volume of distilled water. The administration volume was always 1.05 ml/kg. The positive control group was administered at 1 mg/kg, and was intragastrically administrated 10 days before modeling. 24 hours after the last administration, the rats were anesthetized, injected with EB dye through the side tail vein. Ten minutes later, capsaicin was smeared to velopharyngeal tissue mucosa of rats, wherein each point was smeared for 3 times/5 seconds, with a total of 60 minutes. Blank control group was not subjected to stimulation.

After the end of the experiment, all rats were sacrificed by cervical dislocation, and were subjected to quantitative determination of EB dye exudation at pharyngeal mucosa respectively, in order to evaluate the improvement situation of pharyngeal mucosa inflammation of rats induced by capsaicin. Statistical methods: SPSS 17.0 was used for statistical analysis, the comparison between the groups was analyzed by variance analysis, $P<0.05$ showed that the difference between the groups was statistically significant. See Table 1.

TABLE 1

Effect on rats' pharyngitis of various experimental groups

| groups | N | administration dosage | exudated amount of evans blue (EB) (μg/g) |
|---|---|---|---|
| blank control group | 10 | — | 29.19 ± 2.99 |
| model group | 10 | — | 89.80 ± 3.05 |
| dexamethasone group | 10 | 1 mg/kg | 36.98 ± 2.74*▲ |
| high dose group of Example 1 | 10 | 1.05 ml/kg | 56.54 ± 3.90*▲ |
| medium dose group of Example 1 | 10 | 0.53 ml/kg | 67.66 ± 7.59* |
| low dose group of Example 1 | 10 | 0.18 ml/kg | 81.93 ± 7.44 |
| high dose group of Example 2 | 10 | 1.05 ml/kg | 54.62 ± 4.90*▲ |
| high dose group of Example 3 | 10 | 1.05 ml/kg | 55.54 ± 3.42*▲ |
| high dose group of Example 4 | 10 | 1.05 ml/kg | 54.38 ± 4.01*▲ |
| high dose group of Example 5 | 10 | 1.05 ml/kg | 53.86 ± 3.98*▲ |
| high dose group of Example 6 | 10 | 1.05 ml/kg | 55.37 ± 4.56*▲ |
| high dose group of Comparative Example 1 | 10 | 1.05 ml/kg | 75.66 ± 3.57 |
| medium dose group of Comparative Example 1 | 10 | 0.53 ml/kg | 82.66 ± 4.52 |
| low dose group of Comparative Example 1 | 10 | 0.18 ml/kg | 85.66 ± 4.43 |

Note:
compared with model group,
*indicates P < 0.05,
**indicates P < 0.01, compared with high dose group of Comparative Example 1,
▲indicates P < 0.05;

Compared with blank control group, acute pharyngitis model of model group has been established. Compared with model group, dexamethasone 1 mg/kg group, high, medium dose groups of the medicament produced by Example 1, and high dose groups of the medicaments produced by Example 2-6 can significantly ($P<0.05$) reduce the extravasation of evans blue (EB) in velopharyngeal tissue; moreover, Compared with high dose group of Comparative Example 1, high dose groups of Examples 1-6 of the present application have significant difference ($P<0.05$), indicating that the traditional Chinese medicine composition produced by Example 1 of the present application can significantly improve capsaicin induced rats' pharyngitis symptoms.

Summarizing from the above experimental results, it is indicated that the traditional Chinese medicine composition provided by the present invention can significantly ($P<0.05$) improve capsaicin induced rats' pharyngitis symptoms.

Example 8: Acute Inflammatory Model-Carrageenan-Induced Paw Edema

90 Balb/c male mice (about 8 weeks old) were randomized into 9 groups based on body weight (10 mice/group). The groups were respectively blank control group, model group and positive control group—dexamethasone group, high, medium and low dose groups of the traditional Chinese medicine composition produced by Comparative Example 1 (0.35, 1.05, 2.10 ml/kg), high, medium and low dose groups of the medicament produced by Example 1 (0.35, 1.05, 2.10 ml/kg). Animals from Comparative Example group and Examples of the present application groups were intragastrically administrated 30 days before modeling, once a day. Blank control group and model control group were administered equal volume of distilled water. The administration volume was always 2.10 ml/kg. Dexamethasone group was administered at 10 mg/kg, and was intragastrically administrated 10 days before modeling. The model control group was intragastrically administrated equal volume of distilled water for consecutive 30 days, once a day. On day 30, 1 hour after the test samples were administered, a line was drawn using a marker pen along the external malleolus of right rear paw of rats as the marker. A toe volume measuring instrument was used to measure the volumes of right rear toes of each groups of rats (as the toe volume at 0 hour), and then the right rear toes of rats were subcutaneously injected 1% carrageenan (0.05 mL/rat). The thickness of rat paws at 1, 2, 4 hours were measured respectively. Each animal was measured for 3 times at the same site, and the results were averaged. The swelling value is defined as the difference between the toe volumes measured at different times and the toe volumes before the action of proinflammatory agent, which is used to calculate the toe volume swelling rates at each time period.

[Paw edema (mm)]=[footpad thickness of carrageenan (mm)−footpad thickness of PBS (mm)].

Statistical methods: SPSS 17.0 was used for statistical analysis, the comparison between the groups was analyzed by variance analysis, P<0.05 showed that the difference between the groups was statistically significant. The results are shown in Table 2.

TABLE 2

Effects of carrageenan induced feet swelling of mice in various experimental groups

| groups | N | administration dosage | Swelling degrees of toes at different times after inflammation | | |
|---|---|---|---|---|---|
| | | | 1 h | 2 h | 4 h |
| blank control group | 10 | — | 100 | 100 | 100 |
| model group | 10 | — | 243.99 ± 16.72 | 223.99 ± 14.65 | 203.99 ± 20.77 |
| dexamethasone group | 10 | 10 mg/kg | 177.23 ± 9.67*▲ | 164.17 ± 10.62*▲ | 157.17 ± 12.66*▲ |
| high dose group of Example 1 | 10 | 2.10 ml/kg | 180.23 ± 7.56*▲ | 167.17 ± 8.48*▲ | 166.81 ± 20.37*▲ |
| medium dose group of Example 1 | 10 | 1.05 ml/kg | 223.46 ± 14.74 | 203.89 ± 12.66 | 184.75 ± 7.63 |
| low dose group of Example 1 | 10 | 0.35 ml/kg | 233.90 ± 15.42 | 213.64 ± 12.74 | 197.76 ± 20.37 |
| high dose group of Example 2 | 10 | 1.05 ml/kg | 179.23 ± 12.54*▲ | 170.17 ± 11.48*▲ | 165.31 ± 14.37*▲ |
| high dose group of Example 3 | 10 | 1.05 ml/kg | 183.34 ± 8.23*▲ | 169.17 ± 10.02*▲ | 168.52 ± 11.46*▲ |
| high dose group of Example 4 | 10 | 1.05 ml/kg | 184.21 ± 10.02*▲ | 172.62 ± 12.06*▲ | 164.38 ± 10.67*▲ |
| high dose group of Examples | 10 | 1.05 ml/kg | 186.56 ± 9.18*▲ | 173.33 ± 9.89*▲ | 162.46 ± 10.68*▲ |
| high dose group of Example 6 | 10 | 1.05 ml/kg | 184.63 ± 11.38*▲ | 169.50 ± 10.96*▲ | 162.60 ± 13.20*▲ |
| high dose group of Comparative Example 1 | 10 | 2.10 ml/kg | 223.46 ± 12.12 | 203.89 ± 13.48 | 187.42 ± 8.25 |
| medium dose group of Comparative Example 1 | 10 | 1.05 ml/kg | 238.46 ± 17.31 | 213.89 ± 15.98 | 194.47 ± 5.63 |
| low dose group of Comparative Example 1 | 10 | 0.35 ml/kg | 233.46 ± 18.43 | 213.89 ± 17.42 | 197.64 ± 10.64 |

Note:
compared with model group,
*indicates P < 0.05, compared with high dose group of Comparative Example 1,
▲indicates P < 0.05.

From Table 2, it can be seen that, compared with blank control group, the feet swelling model of model group has been established. Compared with model group, dexamethasone group and high dose groups of the medicaments produced by Examples 1-6 can significantly (P<0.05) reduce carrageenan induced toe swelling degree of mice; moreover, compared with high dose group of Comparative Example 1, high dose groups of Examples 1-6 of the present application have significant difference (P<0.05), indicating that the traditional Chinese medicine composition produced by Example 1 can significantly (P<0.05) improve acute inflammation.

Summarizing from the above experimental results, it is indicated that the traditional Chinese medicine composition provided by the present invention can significantly (P<0.05) reduce carrageenan induced toe swelling degree of mice.

Example 9: Effect on the Mouse Tampon Granuloma

80 Balb/c male mice (about 8 weeks old) were randomized into 8 groups based on body weight (10 mice/group). The groups were respectively model group and positive control group—dexamethasone group, high, medium and low dose groups of the traditional Chinese medicine composition produced by Comparative Example 1 (0.35, 1.05, 2.10 ml/kg), high, medium and low dose groups of the medicament produced by Example 1 (0.35, 1.05, 2.10 ml/kg). Animals from Comparative Example group and Examples of the present application groups were intragastrically administrated 30 days before modeling, once a day. Model control group was administered equal volume of deionized water. The administration volume was always 2.10 ml/kg. Dexamethasone group was administered at 10 mg/kg, and was intragastrically administrated 10 days before modeling. After the last administration, the mice were anesthetized by intraperitoneal injection of 3% pentobarbital sodium at a dose of 60 mg/kg body weight. After anesthesia, the animals were fixed in supine position, and the bilateral inguinal clothing hairs of the rats were removed with a hair removal device. After iodophor disinfection, the rats were subjected to skin incision for about 2 cm at both sides of the groin, and a sterilized tampon was implanted at both sides of the groin of the rats. The incisions were sutured, and the tested samples were continuously administered on the next day, once/day for 7 consecutive days. On the day of completion of the experiment, 1 hour after the administration of tested samples, the rats in each group were anesthetized by intraperitoneal injection of 3% pentobarbital sodium at a dose of 60 mg/kg body weight. After anesthesia, the animals were fixed in supine position, the skin was cut at the original suture. The tampon granulation tissues were peeled and removed with fat removed, placed into clean centrifuge tubes which have been weighed, dried in a unsealed constant temperature drying box at 60° C. for 20 h. Then the tissues were weighted to calculate the net amount of granuloma. The results are shown in Table 3.

The net amount of granuloma (mg)=weight of tampon granuloma after drying−original weight of tampon

TABLE 3

Chronic inflammatory model-cotton pellet-induced granuloma

| groups | N | administration dosage | wet weight of granuloma | Net weight of granuloma |
|---|---|---|---|---|
| model control group | 10 | — | 252.85 ± 4.29 | 17.3 ± 0.46 |
| dexamethasone group | 10 | 10 mg/kg | 217.11 ± 5.59*▲ | 13.03 ± 0.44*▲ |
| high dose group of Example 1 | 10 | 2.10 ml/kg | 220.72 ± 3.06*▲ | 14.17 ± 0.29*▲ |
| medium dose group of Example 1 | 10 | 1.05 ml/kg | 231.02 ± 3.92 | 17.29 ± 1.14 |
| low dose group of Example 1 | 10 | 0.35 ml/kg | 258.47 ± 8.88 | 16.93 ± 0.42 |
| high dose group of Example 2 | 10 | 1.05 ml/kg | 221.32 ± 4.12*▲ | 13.98 ± 0.41*▲ |
| high dose group of Example 3 | 10 | 1.05 ml/kg | 218.74 ± 4.24*▲ | 14.07 ± 0.86*▲ |
| high dose group of Example 4 | 10 | 1.05 ml/kg | 220.96 ± 4.46*▲ | 14.12 ± 1.03*▲ |

TABLE 3-continued

Chronic inflammatory model-cotton pellet-induced granuloma

| groups | N | administration dosage | wet weight of granuloma | Net weight of granuloma |
|---|---|---|---|---|
| high dose group of Example 5 | 10 | 1.05 ml/kg | 224.68 ± 3.98*▲ | 14.30 ± 0.90*▲ |
| high dose group of Example 6 | 10 | 1.05 ml/kg | 222.50 ± 5.03*▲ | 14.68 ± 0.92*▲ |
| high dose group of Comparative Example 1 | 10 | 2.10 ml/kg | 237.42 ± 4.02 | 16.79 ± 1.24 |
| medium dose group of Comparative Example 1 | 10 | 1.05 ml/kg | 253.47 ± 8.88 | 16.93 ± 0.66 |
| low dose group of Comparative Example 1 | 10 | 0.35 ml/kg | 256.47 ± 8.42 | 17.34 ± 0.79 |

Note:
Compared with model group:
*indicates $P < 0.05$; Compared with high dose group of Comparative Example 1,
▲indicates $P < 0.05$.

From Table 3, it can be seen that compared with model control group, dexamethasone group and high dose group of the medicament produced by Example 1 can significantly ($P<0.05$) reduce net weight of granuloma induced by tampon; moreover, compared with high dose group of Comparative Example 1, high dose groups of Examples 1-6 of the present application have significant difference ($P<0.05$), indicating that the traditional Chinese medicine composition produced by Example 1 can significantly ($P<0.05$) inhibit chronic inflammation induced by the cotton pellet-induced granuloma formation.

Summarizing from the above experimental results, it is indicated that the traditional Chinese medicine composition provided by the present invention can significantly ($P<0.05$) inhibit chronic inflammation induced by the cotton pellet-induced granuloma formation.

Example 10: Expectorant Effect in Mice

80 Balb/c male mice (about 8 weeks old) were randomized into 8 groups based on body weight (10 mice/group). The groups were respectively blank control group and positive control group—ammonium chloride group (1 g/kg), high, medium and low dose groups of the traditional Chinese medicine composition produced by Comparative Example 1 (0.35, 1.05, 2.10 ml/kg), high, medium and low dose groups of the medicament produced by Example 1 (0.35, 1.05, 2.10 ml/kg). The blank control group was administered equal volume of deionized water. The administration volume was always 2.10 ml/kg. Gavage was performed for consecutive 30 days, once/day. 30 min before modeling, the positive control group was administered. Mice were fasted for 12 h; 30 min after the last administration, the mice were intraperitoneally injected of 0.5% phenol red solution at 500 mg/kg, After 30 minutes, the mice were scarified, and mouse trachea was isolated, inserted with needle, wherein 5% sodium bicarbonate was injected and rinsed for 3 times (0.5 mL/time). The washing liquids were combined and subjected to measurement of OD value at 546 nm. A certain amount of phenol red was weighted with a balance, and 5% sodium bicarbonate solution was added to formulate 1 ml solution containing 100 g of phenol red, which was diluted sequentially to 1 mL solution containing 0.1, 0.3, 0.7, 1.0, 3.0, 5.0, 10.0 μg of phenol red was measured for absorbance. A standard curve was made by taking the dose of phenol red as abscissa, absorbance as ordinate. The amount of phenol red was calculated from the standard curve of phenol red according to the measured OD value.

The principle of the above mouse phenol red expectorant experiment is: after phenol red was intraperitoneally injected into mice and abdominally absorbed, it can be partially secreted into the airway from bronchial mucus gland. The medicament having expectorant effect can increase the bronchial secretions, and meanwhile, increase the phenol excreted from the mucous membrane of the respiratory tract. Thus, the expectorant effect of a medicament can be observed from the influence of the medicament on excreted amount of phenol red in trachea. Namely, the more phenol red excretes, the better the expectorant effect is.

Experimental Results:

TABLE 4

Expectorant effect in mice of various experimental groups

| groups | N | administration dosage | excreted amount of phenol red (μg/ml) |
|---|---|---|---|
| control group | 10 | — | 5.14 ± 0.35 |
| ammonium chloride group | 10 | 1 g/kg | 7.92 ± 0.88*▲ |
| high dose group of Example 1 | 10 | 2.10 ml/kg | 6.96 ± 0.30*▲ |
| medium dose group of Example 1 | 10 | 1.05 ml/kg | 5.99 ± 0.29 |
| low dose group of Example 1 | 10 | 0.35 ml/kg | 4.82 ± 0.26 |
| high dose group of Example 2 | 10 | 2.10 ml/kg | 7.02 ± 0.41*▲ |
| high dose group of Example 3 | 10 | 2.10 ml/kg | 7.03 ± 1.47*▲ |
| high dose group of Example 4 | 10 | 2.10 ml/kg | 6.90 ± 0.50*▲ |
| high dose group of Example 5 | 10 | 2.10 ml/kg | 6.53 ± 0.62*▲ |
| high dose group of Example 6 | 10 | 2.10 ml/kg | 6.73 ± 0.49*▲ |
| high dose group of Comparative Example 1 | 10 | 2.10 ml/kg | 5.42 ± 0.47 |
| medium dose group of Comparative Example 1 | 10 | 1.05 ml/kg | 5.36 ± 0.21 |
| low dose group of Comparative Example 1 | 10 | 0.35 ml/kg | 5.03 ± 0.46 |

Note:
compared with control group:
*$P < 0.05$; compared with high dose group of Comparative Example 1,
▲indicates $P < 0.05$.

From Table 4, it can be seen that, compared with control group, ammonium chloride group and high dose group of the medicament produced by Example 1 can significantly ($P<0.05$) increase the excreted amount of phenol red; moreover, compared with high dose group of Comparative Example 1, high dose groups of Examples 1-6 of the present application have significant difference ($P<0.05$), indicating that ammonium chloride group and the traditional Chinese medicine composition produced by Example 1 of the present application have obvious expectorant effect ($P<0.05$).

Summarizing from the above experimental results, it is indicated that the traditional Chinese medicine composition provided by the present invention have obvious expectorant effect ($P<0.05$).

Example 11 Clinical Efficacy Trial

After isomaltitol (or fructose syrup, white granulated sugar) was boiled under vacuum, the traditional Chinese medicine composition produced by Example 1 of the present application and edible flavors and fragrances were added to press hard candies.

Recruitment criteria: instituted in accordance with the "technical specifications of inspection and evaluation of health food" (Ministry of health, People's Republic of China, 2003 edition). Subjects having at least one symptom from "dry throat and throat itching, foreign body sensation in the throat, sore throat, burning sensation in the throat, irritable cough accompanied by nausea" in self index; and having at least one symptom from "Pharyngeal hyperemia and edema, retropharyngeal folliculosis, secretions from lateral pharyngeal band and retropharynx, uvula" in physical examination index were recruited.

A total of 101 patients were recruited for clinical trials. The product testing period is two weeks. From the overall situation, it can be seen that the effective rate of the subjects was 64.4% after one week and was up to 87.1% after two weeks.

The comprehensive evaluation of the clinical efficacy showed that the product of the present invention has definite curative effect on chronic pharyngitis, and no obvious toxic and side effects were observed in one patient during the period of taking medicament. It is indicated that the product produced by the traditional Chinese medicine composition produced by the present invention is a medicament that can be used to treat pharyngitis safely and effectively.

The above description gives only the preferred embodiments of the present invention, and it should be noted that for those of ordinary skill in the art, a number of improvements and modifications can be made without departing from the principle of the invention, which are also regarded as falling into the scope claimed in the present invention.

What is claimed is:

1. A method for producing the traditional Chinese medicine composition comprising:
    subjecting TARAXACI HERBA, GLYCYRRHIZAE RADIX ET RHIZOMA, PLATYCODONIS RADIX, CITRI RETICULATAE PERICARPIUNM and PHYLLANTHI FRUCTUS to mixing, water extraction, followed by alcohol precipitation to obtain the traditional Chinese medicine composition.

2. The method according to claim 1, wherein after water extraction and before alcohol precipitation, the method further comprises:
    cooling and filtering the water extract, and concentrating the filtrate to a concentrate with a solid content of 20-50% at 20° C.

3. The method according to claim 1, wherein the alcohol precipitation is performed by adding ethanol to an ethanol concentration of 50-80%, standing for 24 h or more, discarding the filtration residue, concentrating the supernatant to an extractum with a solid content of 60-85% at 20° C.

* * * * *